(12) United States Patent
Hayashizaki (10) Patent No.: US 6,344,345 B1
(45) Date of Patent: Feb. 5, 2002

(54) METHOD FOR PRODUCING DOUBLE-STRANDED DNA WHOSE TERMINAL HOMOPOLYMER PART IS ELIMINATED AND METHOD FOR DETERMINING NUCLEOTIDE SEQUENCE

(75) Inventor: Yoshihide Hayashizaki, Tsukuba (JP)

(73) Assignee: Riken (JP)

( * ) Notice: Subject to any disclaimer, the term of this patent is extended or adjusted under 35 U.S.C. 154(b) by 0 days.

(21) Appl. No.: 09/434,131

(22) Filed: Nov. 5, 1999

(30) Foreign Application Priority Data

Nov. 6, 1998 (JP) ............................................ 10-316102

(51) Int. Cl.[7] .......................... C12P 19/34; C12Q 1/68; C12N 15/00; G01N 33/00; C07H 21/00
(52) U.S. Cl. ...................... 435/91.1; 435/6; 435/91.51; 435/320.1; 436/94; 536/25.3
(58) Field of Search .......................... 435/6, 91.1, 91.2, 435/91.51, 320.1, 183; 436/94; 536/23.1, 24.3, 24.33, 25.3

(56) References Cited

U.S. PATENT DOCUMENTS 5,508,169 A * 4/1996 Deugau et al. ................. 435/6
5,695,937 A * 12/1997 Kinzler et al. ................. 435/6

FOREIGN PATENT DOCUMENTS

WO    WO98/20122    5/1998

OTHER PUBLICATIONS

Xu et al., DNA, vol. 6, No. 5, Oct. 1987 6(5) pp. 505–513, XP002128722.
Okita, Nonradom DNA sequencing of exonuclease III–deleted complementary DNA. Anal. Biochem. 144, 207–211, 1985.*

Cullen, Expression of a cloned human interleukin–2 cDNA is enhanced by the substitution of a heterologous mRNA leader region. DNA, 7, 645–650, 1988.*
Carninci, P. et al, "High–Efficiency Full–Length cDNA Cloning by Biotinylated CAP Trapper", Geonomics, 37, 327–336 (1996).
Carninci, P., et al., "High Efficiency Selection of Full–length cDNA by Improved Biotinylated Cap Trapper", DNA Res. 4, 61–66 (1997).
Stoflet et al., genomic amplification with transcript sequencing. Science 239, 491–494, 1988.*

* cited by examiner

Primary Examiner—Ethan Whisenant
Assistant Examiner—Frank Lu
(74) Attorney, Agent, or Firm—Burnes, Doane, Swecker and Mathis LLP (57) ABSTRACT

Disclosed is a method for producing double-stranded DNA comprising treating double-stranded DNA having a homopolymer part or parts at one or both ends with a restriction enzyme to partly or fully eliminate at least one of the homopolymer part or parts. The restriction enzyme is capable of cleaving double-stranded DNA at a cleavage site separate from a recognition site therefor. Disclosed is a method for determining a nucleotide sequence of double-stranded DNA utilizing one or both strands of the double-stranded DNA as a template, wherein the double-stranded DNA used as the template is double-stranded DNA prepared by the above method of the present invention. The present invention provides a method for producing double-stranded DNA a part or all of which homopolymer part, which may inhibit nucleotide sequence determination, is eliminated, and a method for determining a nucleotide sequence utilizing as a template the double-stranded DNA prepared by the above method of the present invention, whose homopolymer part is partially or fully eliminated.

19 Claims, 2 Drawing Sheets

SEQUENCE LISTING

```
<160> NUMBER OF SEQ ID NOS:  14

<210> SEQ ID NO 1
<211> LENGTH: 18
<212> TYPE: DNA
<213> ORGANISM: BbvI enzyme
<220> FEATURE:
<221> NAME/KEY: misc_feature
<222> LOCATION: (6)..(18)
<223> OTHER INFORMATION: Nucleotides 6-18 are n wherein n = any
      nucleotide.

<400> SEQUENCE: 1
gcagcnnnnn nnnnnnnn                                                   18

<210> SEQ ID NO 2
<211> LENGTH: 18
<212> TYPE: DNA
<213> ORGANISM: BbvI enzyme
<220> FEATURE:
<221> NAME/KEY: misc_feature
<222> LOCATION: (6)..(18)
<223> OTHER INFORMATION: Nucleotides 6-18 are n wherein n = any
      nucleotide.

<400> SEQUENCE: 2
cgtcgnnnnn nnnnnnnn                                                   18

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence:
      hemimethylated cDNA
<221> NAME/KEY: misc_feature
<222> LOCATION: (14)
<223> OTHER INFORMATION: Nucleotide 14 is n wherein n = any nucleotide.
```

```
<400> SEQUENCE: 3
gggggggggg gggnmtttttt ttttttttgag ctcga                    35

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence:
      hemimethylated cDNA

<400> SEQUENCE: 4
gcagcccccc ccccccccaaa aaaaaaaaac tcgagct                   37

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence:
      hemimethylated cDNA
<221> NAME/KEY: misc_feature
<222> LOCATION: (18)
<223> OTHER INFORMATION: Nucleotide 18 is n wherein n = any nucleotide.

<400> SEQUENCE: 5
cgtcgggggg ggggggggnmt tttttttttt tgagctcga                 39

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      hemimethylated cDNA

<400> SEQUENCE: 6
ccccaaaaaa aaaaaactcg agct                                  24

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:
      hemimethylated cDNA
<221> NAME/KEY: misc_feature
<222> LOCATION: (1)
<223> OTHER INFORMATION: Nucleotide 1 is n wherein n = any nucleotide.

<400> SEQUENCE: 7 nmttttttttt ttttgagctc ga                                   22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      hemimethylated cDNA

<400> SEQUENCE: 8
aaaaaaaaaa aactcgagct                                       20

<210> SEQ ID NO 9
<211> LENGTH: 22
<212> TYPE: DNA
```

<213> ORGANISM: Artificial Sequence
<220> FEATURE:
<223> OTHER INFORMATION: Description of Artificial Sequence:
      hemimethylated cDNA
<221> NAME/KEY: misc_feature
<222> LOCATION: (1)
<223> OTHER INFORMATION: Nucleotide 1 is n wherein n = any nucleotide.

<400> SEQUENCE: 9
nmtttttttt ttttgagctc ga                                         22

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      hemimethylated cDNA
<221> NAME/KEY: misc_feature
<222> LOCATION: (2)..(4)
<223> OTHER INFORMATION: Nucleotides 2-4 are n wherein n = any
      nucleotide.

<400> SEQUENCE: 10
cnnnaaaaaa aaaaaactcg agct                                       24

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:
      hemimethylated cDNA
<221> NAME/KEY: misc_feature
<222> LOCATION: (5)..(8)
<223> OTHER INFORMATION: Nucleotides 5-8 are n wherein n = any
      nucleotide.

<400> SEQUENCE: 11
taagnnnnmt tttttttttt tgagctcga                                  29

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:
      hemimethylated cDNA
<221> NAME/KEY: misc_feature
<222> LOCATION: (2)..(4)
<223> OTHER INFORMATION: Nucleotides 2-4 are n wherein n = any
      nucleotide.

<400> SEQUENCE: 12
cnnnaaaaaa aaaaaac                                               17

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:
      hemimethylated cDNA
<221> NAME/KEY: misc_feature
<222> LOCATION: (5..(8)
<223> OTHER INFORMATION: Nucleotides 5-8 are n wherein n = any
      nucleotide.

<400> SEQUENCE: 13
taagnnnnmt tttttttttt tgagctc                                    27

```
<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: 50-mer
      oligonucleotide

<400> SEQUENCE: 14
gagagaggga cgcagcgacg cgcatcacct gcgagagaga gagagagaga            50
```

METHOD FOR PRODUCING DOUBLE-STRANDED DNA WHOSE TERMINAL HOMOPOLYMER PART IS ELIMINATED AND METHOD FOR DETERMINING NUCLEOTIDE SEQUENCE

This application claims priority under 35 U.S.C. §§119 and/or 365 to 316102/1998 filed in Japan on Nov. 6, 1998; the entire content of which is hereby incorporated by reference.

BACKGROUND OF THE INVENTION

1. Field of the Invention

The present invention relates to a method for producing double-stranded DNA whose terminal homopolymer part has been partly or fully eliminated, and a method for determining nucleotide sequence using double-stranded DNA obtained by the foregoing method.

2. Related Art

In addition to preparation of full-length cDNA libraries, nucleotide sequence determination is also an essential technique for analyzing a gene transcript as a functional unit in the medical and biological fields. For identification of genes and functional analyses thereof, it is extremely important to obtain cDNA clones, of which number is said to be about one hundred of thousands in humans and mice, and to identify their locations on genomes.

A number of methods have been proposed for the preparation of cDNA libraries. The inventors of the present invention proposed a method affording high synthesis efficiency of full-length cDNA, which will be explained below, and are continuing further studies for practical use of the method.

In that method, a first cDNA strand is synthesized by using poly (A) RNA as a template, and oligo dT having a specific restriction enzyme site in the 5' end sequence and an anchor site in the 3' end sequence as a primer, and an oligo dG is added to the 3' end of the obtained first cDNA strand using an enzyme such as terminal deoxynucleotidyl transferase. Then, a second cDNA strand is synthesized by using oligo dC having a restriction site in the 5' end sequence as a primer. Those strands are introduced into a vector using the restriction sites present at the both ends of the cDNA. The process is elaborated so that only the restriction sites at the both ends should be cleaved during the introduction into the vector by using methylated DCTP instead of DCTP as a substrate for the synthesis of the first cDNA strand, and using a restriction enzyme sensitive to hemimethylation. The detail of the protocol for preparing full length cDNA libraries by such a method is described in WO 98/20122; Carninci, P. et al., Genomics, 37, 327–336 (1996); Carninci, P. et al., DNA Res., 4, 61–66 (1997) and the like, and an enormous number of full length cDNA clones have actually been obtained. Moreover, the analyses of nucleotide sequences of the obtained full length cDNA clones are well under way. The locations of cDNA on genomes are identified by these works.

However, cDNA in such a cDNA library as obtained by the aforementioned method has homopolymers of oligo dA:dT and oligo dG:dC at the both ends. That is, one strand of the double-stranded cDNA excised from the vector with a restriction enzyme has oligo dA:dT, and the other has oligo dG:dC (usually 11 to 16 base pairs). The oligo dA: dT originates from the poly A chain, which is originally possessed by mRNA, and the oligo dG:dC originates from a dG tailing, which is introduced during the production of double-stranded DNA as a site to which the primer is attached.

However, it was found that, when the sequencing was performed by using the double-stranded cDNA as a template to determine its nucleotide sequence, the aforementioned homopolymer part inhibited the sequencing. As the sequencing method using double-stranded cDNA as a template, there are the dideoxy method using a DNA polymerase based on the Sanger method, and the transcript sequencing method using an RNA polymerase, which was developed by the inventors of the present invention. Both of these methods determine a nucleotide sequence based on terminal nucleotides and chain lengths of reaction products obtained in the presence of terminators interrupting the chain elongation by polymerase.

However, the presence of a homopolymer part at the end of double-stranded cDNA causes a problem that reading of the sequence becomes to be difficult. The cause of this problem is not necessarily certain. Furthermore, when the double-stranded cDNA is amplified by PCR before the sequencing, the polymerase may fail to correctly reflect the length (repeating nucleotide number) of the homopolymer part in the synthesis. Thus, there may be obtained fragments of different lengths having a certain nucleotide as the terminal, which must have the same lengths. This means that fragments of a certain length contain those having different terminal nucleotides, and it makes the sequencing impossible. In particular, when double-stranded cDNA having oligo dG:dC at one or both ends is used as the template, this tendency is more strongly observed.

It has been turned out that the aforementioned problem is very serious in the nucleotide sequence determination of DNA. Moreover, the aforementioned problem makes it difficult to determine a nucleotide sequence efficiently, rapidly, and accurately for an enormous number of clones in a cDNA library, and it also makes it difficult to identify a location of each gene in a genome.

The above problem may be alleviated to some extent by using oligo dA:dT and oligo dG:dC of a shorter chain length. However, it is not easy to use oligo dA:dT and oligo dG:dC of a shorter chain length in the actual reaction. As mentioned above, the oligo dA:dT originates from the poly A chain originally possessed by mRNA, and therefore it is theoretically possible to make the oligo dA:dT shorter by using a shorter oligo dT in the primer used for the transcription reaction. However, a shorter oligo dT in the primer may disadvantageously reduce the yield of transcription products, and thus it is not practical. On the other hand, the oligo dG:dC originates from a dG tailing, which is introduced during the production of double-stranded DNA as a site to which a primer is attached, and therefore it is also theoretically possible to make the oligo dG:dC shorter by using a shorter oligo dG tailing. However, it is also actually difficult to control the chain length of the dG tailing within a desired range.

SUMMARY OF THE INVENTION

Therefore, the object of the present invention is to provide a method for preparing double-stranded cDNA whose terminal homopolymer part, which may inhibit the nucleotide sequence determination, has been partly or fully eliminated.

A further object of the present invention is to provide a method for determining nucleotide sequence using as a template double-stranded DNA obtained by the foregoing method, i.e., double-stranded cDNA whose terminal homopolymer part or parts has been partly or fully eliminated.

The present invention relates to a method for producing double-stranded DNA comprising treating double-stranded DNA having a homopolymer part or parts at one or both ends with a restriction enzyme to partly or fully eliminate at least one of the homopolymer part or parts, wherein the restriction enzyme is capable of cleaving double-stranded DNA at a cleavage site separate from a recognition site therefor.

The present invention further relates to a method for determining a nucleotide sequence of double-stranded DNA utilizing one or both strands of the double-stranded DNA as a template, wherein the double-stranded DNA used as the template is double-stranded DNA prepared by the aforementioned method of the present invention.

According to the present invention, a nucleotide sequence of cDNA clone can be accurately determined by eliminating a part or whole of homopolymer that exists at a DNA terminus.

PREFERRED EMBODIMENTS OF THE INVENTION

The method for producing double-stranded DNA according to the present invention is characterized in that double-stranded DNA having a homopolymer part or parts at one or both ends is treated with a restriction enzyme cleaving double-stranded DNA at a cleavage site separate from a recognition site therefor to partly or fully eliminate at least one of the homopolymer part or parts.

The double-stranded DNA having a homopolymer part or parts at one or both ends, which is to be treated with this invention includes double-stranded DNAs having a homopolymer part of oligo dG:dC or oligo dA:dT at one end. The double-stranded DNA also includes double-stranded DNAs having a homopolymer part of oligo dG:dC or oligo dA:dT at one end and a homopolymer part of oligo dG:dC or oligo dA:dT at the other end. In the case of double-stranded DNA having homopolymer parts at both ends, in general, if the homopolymer of one end is oligo dA:dT, that of the other end is dG:dC. However, double-stranded DNA may have at both ends homopolymer parts of oligo dG:dC or homopolymer parts of oligo dA:dT. The chain length of the homopolymer part is not particularly limited and is generally in a range of 5–20. A restriction enzyme cleaving double-stranded DNA at a cleavage site separate from a recognition site therefor may be selected in view of the length of the homopolymer part. When the homopolymer is partly eliminated, the chain length of the remaining homopolymer is determined considering facility of sequence determination of the resulting DNA.

The method for producing double-stranded DNA according to the present invention utilizes a restriction enzyme cleaving double-stranded DNA at a cleavage site separate from a recognition site therefor. The "restriction enzyme cleaving double-stranded DNA at a cleavage site separate from a recognition site therefor" means a restriction enzyme that cleaves double-stranded DNA at a cleavage site on the DNA, which is far from a recognition site for the restriction enzyme. As such a restriction enzyme, for example, class IIS restriction enzymes have been known.

For example, BbvI, one of the class IIS restriction enzymes, acts on double-stranded DNA having a recognition site which consists of 5'-GCAGC and its complementary strand, and a cleavage site (▼▲) at a location separating from the recognition site as shown below.

| 5' -GCAGC NNNNNNNN▼NNNN-N | (SEQ ID NO: 1) |
|---|---|
| CGTCG NNNNNNNN-NNNN▲N | (SEQ ID NO: 2) |

Specific examples of the class IIS restriction enzymes include, for example, AlwI, AlwXI, Alw26I, BbsI, BbvI, BbvII, BcefI, BccI, BcgI, BciVI, BinI, BmrI, BpmI, BsaI, BseRI, BsgI, BsmAI, BsmBI, BspMI, BsrDI, BstF5I, EarI, Eco3lI, Eco57I, Esp3I, Esp3I, FauI, FokI, GsuI, HgaI, HinGUII, HphI, Ksp632I, MboII, MmeI, MnlI, NgoVIII, PleI, RleAI, SapI, SfaNI, TaqII, TthlllII, BsmIs, BsrIs, BsmFI, BseMII and the like (see Szybalski, W. et al., Gene, 100, 13–26 (1991); and New England Biolab, Inc., Catalog: http://www.neb.com).

Recognition sites and cleavage sites of several restriction enzymes are as follows (parenthesized are recognition site and cleavage site): BbvI (GCAGC 8/12), HgaI (GACGC 5/10), BsmFI (GGGAC 10/14), SfaNI (GCATC 5/9), and BspM I (ACCTGC 4/8).

According to the preparation method of the present invention, double-stranded DNA having a homopolymer part or parts at one or both ends is used as a starting material to prepare double-stranded DNA at least one of which homopolymer part is partly or fully eliminated. The starting material, double-stranded DNA having a homopolymer part or parts at one or both ends, can be prepared by, for example, the methods disclosed in WO 98/20122; Carninci, P. et al., Genomics, 37, 327–336 (1996); Carninci, P. et al., DNA Res., 4, 61–66 (1997) or the like. However, the preparation method of the present invention utilizes the aforementioned restriction enzyme cleaving double-stranded DNA at a cleavage site separate from a recognition site therefor. Thus it is necessary to use double-stranded DNA having a recognition site for the restriction enzyme at the end of the homopolymer part. Such double-stranded DNA can be prepared by using as primers the homopolymer and another sequence containing the sequence of the recognition site that is not the homopolymer.

The double-stranded DNA to be treated with the restriction enzyme may be, for example, double-stranded cDNA. Further, the double-stranded DNA to be treated with the restriction enzyme may also be artificially modified double-stranded cDNA or chemically synthesized double-stranded DNA.

Furthermore, as the double-stranded DNA to be treated with the restriction enzyme, one having chemical modification in a part of one of the strands other than the homopolymer part may also be used. The chemical modification may be, but not particularly limited to, modification by methylation. The method for the methylation is well-known to those skilled in the art, and a method utilizing a methylated nucleic acid as a substrate for the synthesis of the first strand of the double-stranded DNA or the like can be used. Such chemical modification can be introduced into any nucleic acid. Since methylated cytosine and methylated adenine exist in nature, and methylated cytosine is commercially available, methylated cytosine and methylated adenine are preferably used.

In order to amplify full-length cDNA in the preparation of a full-length cDNA library, a host is transformed with a plasmid carrying double-stranded cDNA. Thus at least one end of the double-stranded cDNA must be a cohesive end. However, if the cDNA contains a cleavage site for the restriction enzyme used for the preparation of the sticky end, the double-stranded cDNA itself may be cleaved during the preparation. Therefore, in order to prevent such cleavage of the double-stranded cDNA during the introduction of sticky end, there has been proposed a method utilizing methylation of one strand of the double-stranded cDNA and a hemimethylation-sensitive restriction enzyme for the introduction of sticky end (Carninci, P. et al., Genomics, 37, 327–336 (1996); Carninci, P. et al., DNA Res., 4, 61–66 (1997)). In this method, methylation is introduced into one strand of double-stranded cDNA during the preparation of a full-length cDNA library by introducing a homopolymer part having a specific restriction site into the both ends, provided that a primer without methylation is used for the sequence for the preparation of sticky end. As a result, when a hemimethylation-sensitive restriction enzyme is allowed to act on such double-stranded cDNA introduced with the methylation into its one strand, the internal restriction site of the cDNA is not cleaved, but a sticky end is formed due to the primer without methylation. This method utilizing the introduction of hemimethylation into cDNA is based on the method for differentiating restriction enzyme sensitivity as for primer/linker sites and internal sites of cDNA during the cDNA synthesis (Huse, W. D. et al., U.S. Pat. No. 5,681,726 (1997)).

Also in the preparation method of the present invention, a hemimethylated cDNA in which one strand is methylated can be used as the double-stranded DNA to be treated with a restriction enzyme. However, while a number of restriction enzymes exhibiting sensitivity to methylation for the both strands have been known, few restriction enzymes have been known as those exhibiting sensitivity to the hemimethylation. Restriction enzymes exhibiting sensitivity to methylation for the both strands do not necessarily exhibit sensitivity to hemimethylation (Paroush, Z. et al., Cell, 63, 1229–1237 (1990) ). Therefore, according to the present invention, when the double-stranded DNA to be treated with a restriction enzyme is a hemimethylated cDNA one of which strand has been methylated, a restriction enzyme sensitive to hemimethylation is used as the restriction enzyme cleaving double-stranded DNA at a cleavage site separate from a recognition site therefor.

As long as the investigation is carried out under the conditions mentioned in the example described hereinafter, among the aforementioned class IIS restriction enzymes, at least BbvI (GCAGC 8/12), HgaI (GACGC 5/10) and GsuI (CTGGAG 16/14) are sensitive to the hemimethylation (parenthesized are recognition site and cleavage site).

Figure 2:
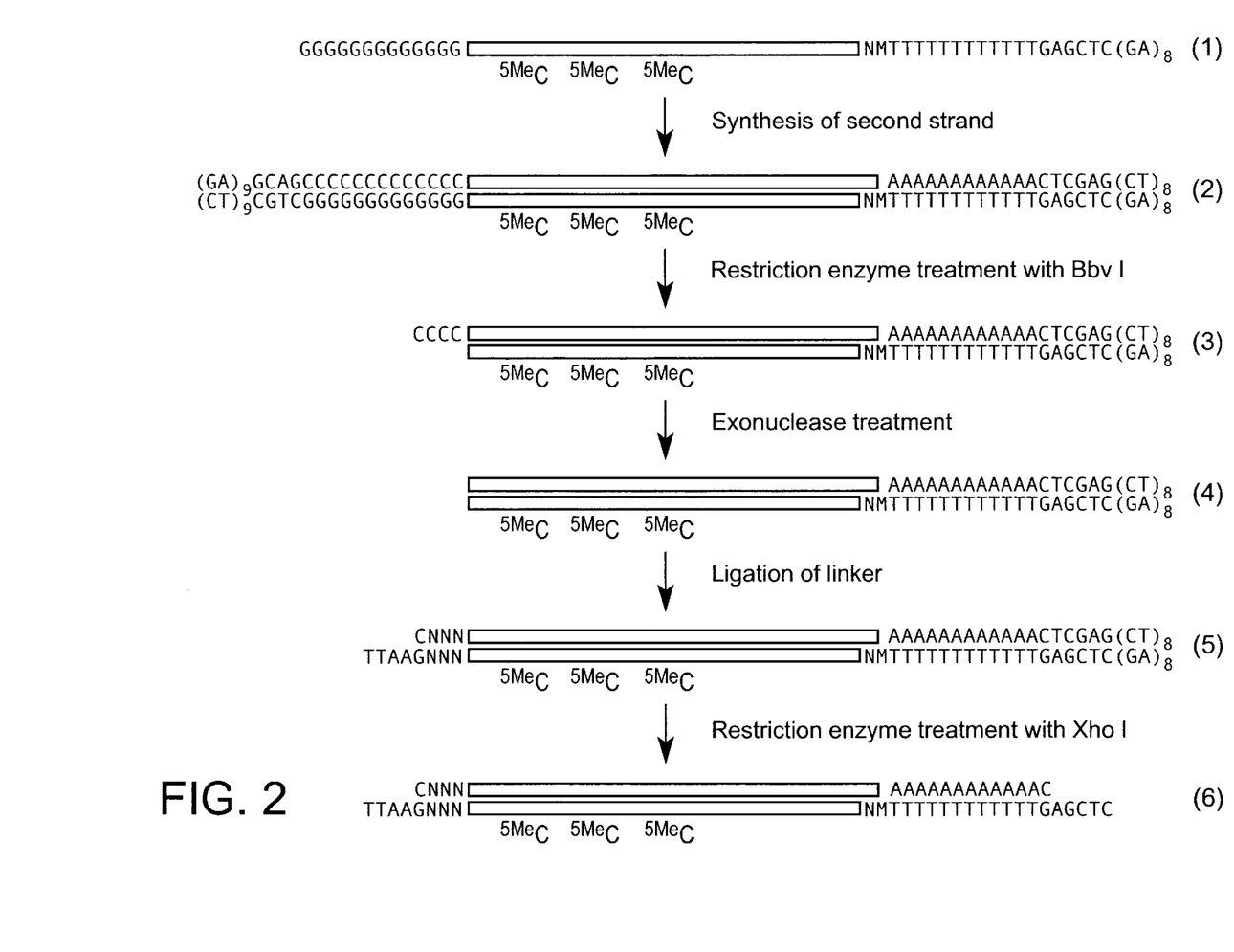
FIG. 2 represents one possible scheme for producing double-stranded DNA according to the present invention.

The method for preparing double-stranded DNA whose terminal homopolymer is eliminated will be explained hereinafter with reference to the scheme illustrated in FIG. 2, which exemplifies a case of hemimethylated cDNA (Seq ID No.s 3–13).

Single-stranded DNA (1) is prepared. The singlestranded DNA (1) has hemimethyl groups which have been partially introduced into a part other than the homopolymer. The single-stranded DNA (1) has oligo dG at the 3' end and oligo dT at the 5' end. The single-stranded DNA (1) can be prepared by, for example, the methods described in Carninci, P. et al., Genomics, 37, 327–336, (1996) Carninci, P. et al., DNA Res., 4, 61–66 (1997) or the like. In the above scheme, single-stranded DNA having oligo dG at the 3' end and oligo dT at the 5' end is exemplified. However, the present method can be applied to single-stranded DNAs having other oligo chains as the homopolymers.

Then, double-stranded DNA (2) having homopolymer parts is prepared by using the single-stranded DNA (1) as a template, and a homopolymer complementary to oligo dG of the singlestranded DNA (1) as a primer. In this case, the primer has at the 5' end a non-homopolymer sequence which contains a recognition sequence for a restriction enzyme used for the elimination of the homopolymer part, for example, BbvI (see the above scheme). The homopolymer part of at one end of the synthesized double-stranded DNA (2) (left side of DNA(2) in the scheme) is composed of the homopolymer consisting of oligo dG:dC and the non-homopolymer containing the recognition sequence for the aforementioned restriction enzyme such as BbvI. Another end of the synthesized double-stranded DNA (2) (right side of DNA (2) in the scheme) is composed of the homopolymer consisting of oligo dA:dT and a non-homopolymer. The nonhomopolymer may contain a recognition sequence for a restriction enzyme. In this case, any restriction enzyme selected from Class II enzymes including class IIS enzymes can be used. If the non-homopolymer attached to the oligo dA:dT contains a restriction site for a restriction enzyme used for eliminating the homopolymer part of the left side such as BbvI, both ends of double-stranded DNA (2) can be cleaved simultaneously.

The aforementioned double-stranded DNA (2) is treated with a restriction enzyme cleaving double-stranded DNA at a cleavage site separate from a recognition site therefor, BbvI in the scheme to eliminate a part or whole of the homopolymer part of the left side. As a result, double-stranded DNA (3) whose homopolymer part is eliminated can be obtained.

The obtained double-stranded DNA (3) can be amplified by introducing it into a plasmid vector and culturing a host transformed with the plasmid. To this end, a linker with an extruded end of DGGGG is ligated to the obtained double-stranded DNA (3) The linker has at the opposite site of the oligo dG a cohesive end for EcoRI for easy introduction to a vector. By the ligation of the above linker to the DNA (3), double-stranded DNA (5) with a cohesive end for a restriction enzyme. In this case, preparation of DNA (4) is skipped.

Alternatively, the double-stranded DNA (3) can be treated as follows. The single-stranded DNA of its end (left side of DNA (3)) produced by the restriction enzyme treatment is specifically digested with an enzyme that has exonuclease activity specifically exerted on single-stranded DNA to obtain double-stranded DNA (4) with a blunt end. A suitable linker such as a linker having a cohesive end for EcoRI is ligated to the blunt end of the DNA (4) to form double-stranded DNA (5) with a cohesive end.

The right end of the resulting double-stranded DNA (5) (the end not processed with the restriction enzyme BbvI (dA:dT homopolymer end in the scheme)) is treated with a suitable restriction enzyme such as XhoI. Any restriction enzyme selected from Class II enzymes including class IIS enzymes can be used. The obtained double-stranded DNA can be introduced into a suitable vector and amplified.

In addition to the above methods, the obtained double-stranded DNA (2) may be amplified by PCR using the double-stranded DNA (2) as a template.

The length of the homopolymer eliminated by the aforementioned process is determined depending on the kind of the used restriction enzyme cleaving double-stranded DNA at a cleavage site separate from a recognition site therefor. Thus the restriction enzyme may be suitably selected considering the length of the homopolymer contained in the homopolymer part. Further, the sequence of the nonhomopolymer part containing the recognition site for the restriction enzyme can be suitably selected depending on the kind of restriction enzyme to be used.

Furthermore, by using a restriction enzyme not acting on double-stranded DNA having chemical modification in its recognition site or cleavage site, only the homopolymer part or parts at one or both ends of the double-stranded DNA can be eliminated, even if a recognition site for the restriction enzyme is contained in the double-stranded DNA. As such a restriction enzyme, a restriction enzyme that does not act on a site of double-stranded DNA having a methyl group as chemical modification can be used. Partially introducing methyl groups as chemical modification into double-stranded DNA other than the homopolymer part and using such a restriction enzyme prevent cleavage of the double-stranded DNA. Examples of the restriction enzyme that does not act on a site of double-stranded DNA having a methyl group as chemical modification include BbvI, HgaI and GsuI.

Method for Determining Nucleotide Sequence

The method for determining nucleotide sequence according to the present invention is a method for determining nucleotide sequence of double-stranded DNA utilizing one or both of strands of the double-stranded DNA as a template, and characterized in that the double-stranded DNA used as the template is double-stranded DNA prepared by the method according to the present invention explained above.

More precisely, in the method of the present invention, a nucleotide sequence of double-stranded DNA whose homopolymer part or parts at one or both ends is (are) eliminated is determined by utilizing one or both of strands of the double-stranded DNA as the template. The double-stranded DNA used as the template should be used as the template after amplified by microorganisms or PCR. Both of the methods for amplification are well known in the art. When double-stranded DNA used as the template is amplified by PCR, a part or whole of the oligo dG:dC of the double-stranded DNA is preferably eliminated.

As the sequencing method utilizing double-stranded DNA as a template, for example, the dideoxy method using a DNA polymerase based on the Sanger method, the transcript sequencing method using an RNA polymerase (disclosed in, for example, WO 96/14434) and the like can be used. Both of these methods determines a nucleotide sequence based on terminal nucleotides and chain lengths of reaction products obtained in the presence of terminators interrupting the chain elongation by polymerase.

The determination of nucleotide sequence can be attained by, for example, preparing nucleic acid transcripts of double-stranded DNA in the presence of terminators for the nucleic acid transcription, and analyzing the obtained nucleic acid transcripts. As an enzyme catalyzing the aforementioned nucleic acid transcription, an RNA polymerase can be used. The transcript sequencing method using an RNA polymerase is particularly preferred, since the product amplified by PCR can be sequenced without purification, and it enables quick sequencing with a small amount of sample.

The transcript sequencing method is a method for determining a nucleotide sequence comprising, for example, allowing reactions of one or more of ribonucleoside-5'triphosphates including ATP, GTP, CTP, UTP and derivatives thereof, and 3'-deoxyribonucleoside-5'-triphosphates (3'dNTPs) including 3'-dATP, 3'-dGTP, 3'-dCTP, 3'-dUTP, and derivatives thereof in the presence of an RNA polymerase and DNA fragments containing a promoter sequence for the RNA polymerase to obtain nucleic acid transcription products, separating the obtained products, and reading the nucleotide sequence from the separated fraction. The DNA fragment (double-stranded DNA) used as the template contains a promoter sequence for the aforementioned RNA polymerase.

Further, mutant RNA polymerases which consist of a wild-type RNA polymerase at least one of which amino acid is modified so that its ability to incorporate the aforementioned 3'-DNTP derivatives should be increased compared with that of the corresponding wild-type RNA polymerase or any other wild-type RNA polymerases.

In the method for determining nucleotide sequence of the present invention, double-stranded DNA in which the homopolymer part, which may inhibit the sequence reading, is partially or fully eliminated is used as the template. Thus the accuracy of the nucleotide sequence determination can be improved.

EXAMPLES

The present invention will be further explained hereinafter with reference to the following examples.

Example 1

An oligodeoxyriboside 50-mer: 5'-GAGAGAGGGACGCAGCGAC GCGCATCACCTGC-GAGAGAGAGAGAGAGA (oligo I) and its complementary strand (oligo II) containing a recognition site for each of BbvI (GCAGC 8/12), HgaI (GACGC 5/10), BsmFI (GGGAC 10/14), SfaNI (GCATC 5/9), and BspMI (ACCTGC 4/8) among class IIS restriction enzymes (parenthesized are recognition site and cleavage site) were prepared (ESPEC OLIGO SERVICE). Metylated oligo I (m-oligo I) and methylated oligoII (m-oligo II) were also prepared by using 5-methylcytosine instead of cytosine (ESPEC OLIGO SERVICE). These oligomers were used after purification by polyacrylamide gel electrophoresis (Sambrook, J. Fritsch, E. F. and Maniatis, T., Molecular Cloning: A Laboratory Manual, 2nd Ed. 1989, Cold Spring Harbor Laboratory). Two kinds of oligomers were labeled and annealed by using RI labels and DNA 5' end labeling kit (TAKARA MEGALABEL) utilizing T4 polynucleotide kinase and $\gamma_{-12}$ P-ATP (Amersham). Two kinds of the oligomers (10 µg each) in each of the following combinations were added to 20 µl of reaction mixture. The combinations consisted of following four kinds of combinations: 1) oligo I+oligo II, 2) m-oligo I+oligo II, 3) oligo I+m-oligo II, and 4) m-oligo I+m-oligo II. After the reaction, the kinase was inactivated by a heat treatment at 65° C. for 20 minutes, each reaction mixture was gradually cooled at 45° C. for 20 minutes and then at 37° C., and double-stranded oligomers were collected in a spin column.

The collected double-stranded oligomers (100 ng) was added with 0.5 or 5 units of one of the five kinds of the class IIS restriction enzymes (BbvI, HgaI, BsmFI, SfaNI, and BspMI, all produced by New England Biolabs), and restriction enzyme treatment was performed at 37° C. for 1 hour (20 µl of the reaction mixture, the reaction composition except for enzyme and oligomer was according to the attached instruction of New England Biolabs). Then, the reaction mixture (3 µl) was subjected to polyacrylamide gel electrophoresis, and bands were detected by Bioimaging Analyzer BAS2000.

Figure 1:
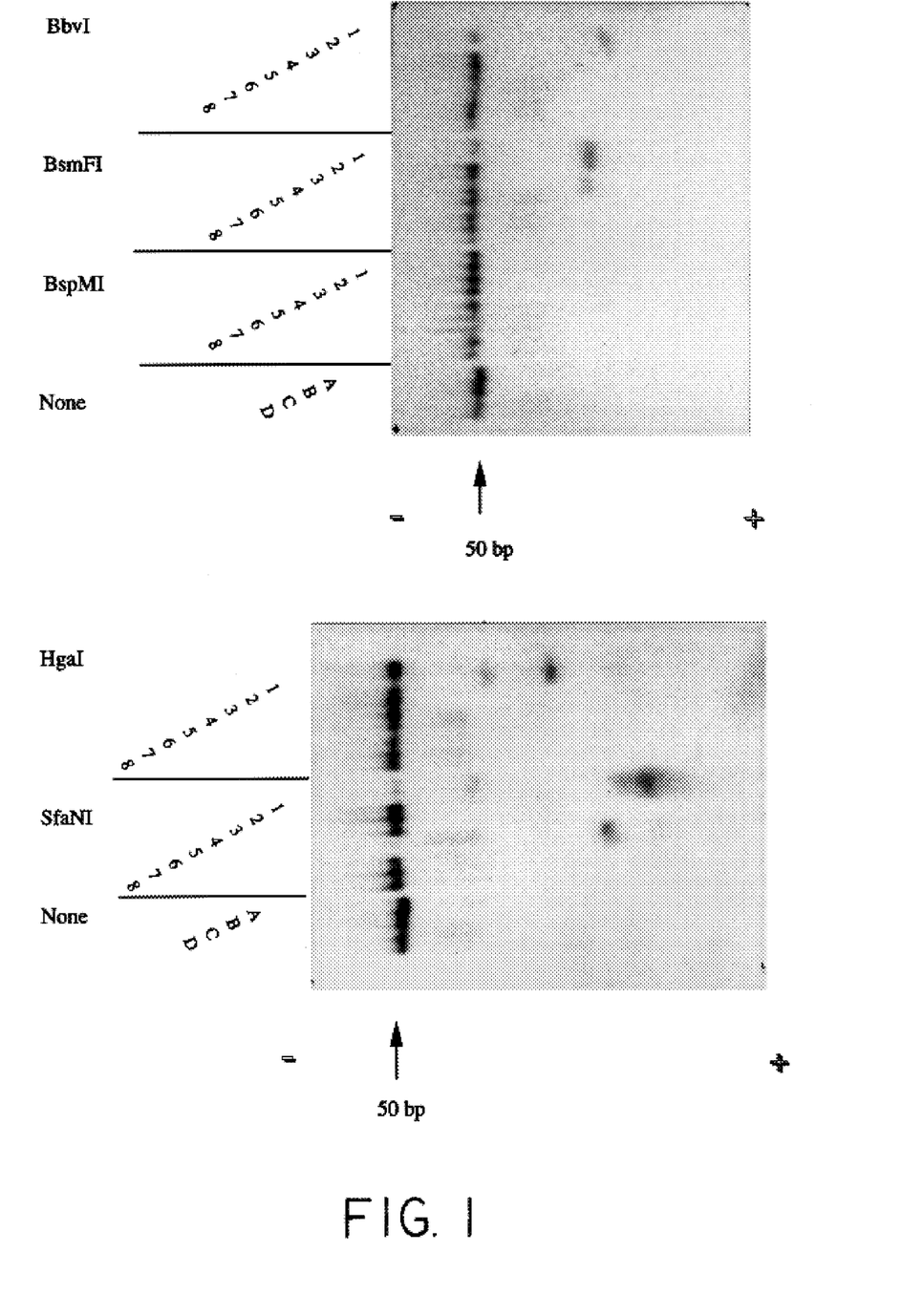
FIG. 1 represents a gel electrophoresis pattern for double-stranded oligodeoxyriboside 50-mer subjected to a restriction enzyme treatment. As restriction enzymes, BbvI, BsmFI, BspMI, HgaI, and SfaNI were used. The concentrations used were 0.5 units for Lanes 1, 3, 5, and 7, and 5 units for Lanes 2, 4, 6, and 8. As the double-stranded oligomers, used were 100 ng each of oligo I+oligo II for Lanes 1 and 2, m-oligo I+oligo II for Lanes 3 and 4, oligo I+m-oligo II for Lanes 5 and 6, and m-oligo I+m-oligo II for Lanes 7 and 8. The letters of A, B, C, and D indicate the migration locations of double-stranded oligodeoxyribosides, oligo I+oligo II, m-oligo I +oligo II, oligo I+m-oligo II, and m-oligo I+m-oligo II, respectively, when they were not subjected to the restriction enzyme treatment.

As a result, as for BbvI, the oligomers were not cleaved in Lanes 3 to 8 as shown in FIG. 1, and thus they were sensitive to methylation including hemimethylation. As for HgaI, the oligomer was not cleaved in Lane 1, whereas it was cleaved in Lane 2. Therefore, HgaI functioned as a restriction enzyme when its concentration was controlled. However, it was sensitive to methylation including hemimethylation since the oligomers were not cleaved in Lanes 3 to 8. In contrast, as for BspMI, the oligomers were not cleaved in any of Lanes 1 to 8, and it was turns out that it did not work as a restriction enzyme under the conditions of this example. As for BsmFI and SfaNI, they cleaved the oligomers in Lanes 1 and 2, and cleaved the hemimethylated oligomer in Lane 4. Thus, they were not found to be completely sensitive to hemimethylation.

Therefore, it is possible to eliminate at least a part or whole of the homopolymer present at an end of double-stranded DNA using BbvI, BsmFI, HgaI, or SfaNI. However, when a recognition site for a class IIS restriction enzyme to be used is contained in the double-stranded DNA, the double-stranded DNA must be protected by chemical modification such as methylation, since it may be otherwise cleaved by the restriction enzyme. Therefore, when hemimethylated double-stranded DNA is used in order to protect the double-stranded DNA from cleavage, a part or whole of homopolymer part at its end can be eliminated by using BbvI and HgaI, which were demonstrated to be sensitive to hemimethylation by the above experiments, without cleaving the double-stranded DNA. In addition, it has been demonstrated by other experiments that GsuI can also be used as the restriction enzyme in place of BbvI and HgaI.

The nucleotide sequence determination of a full-length cDNA library can be performed more quickly and correctly by, for example, preparing the cDNA library as follows. That is, as shown in the above scheme, full length cDNA whose homopolymer ends are introduced with a restriction enzyme site for BbvI, HgaI, GsuI or the like is prepared, treated with a restriction enzyme such as BbvI, HgaI and GsuI to remove the homopolymer, and ligated with a linker required for cloning to obtain a full length cDNA library. More specifically, a full length cDNA library can be prepared by treating cDNA with a restriction enzyme such as BbvI, HgaI and GsuI, ligating to the resulting extruded end a linker with a cohesive end for EcoRI or the like, and cloned into a suitable vector. Alternatively, a full length cDNA library can be prepared by treating cDNA with a restriction enzyme such as BbvI, HgaI and GsuI, making a blunt end through treatment with S1 nuclease or the like, ligating with a linker having an cohesive end for EcoRI or the like, and cloned into a suitable vector.

What we claimed is:

1. A method for producing double-stranded DNA comprising:
   providing single-stranded DNA comprising a homopolymer at one or both ends;
   employing said single-stranded DNA to produce a double-stranded DNA comprising a homopolymer at one or both ends;
   wherein the double-stranded DNA does not contain internal type IIS restriction sites or is chemically modified in order to protect the double-stranded DNA from internal type IIS restriction enzyme cleavage;
   after producing said double-stranded DNA, treating said double-stranded DNA comprising a homopolymer at one or both ends with a type IIS restriction enzyme to partly or fully eliminate at least one of the homopolymers, wherein the restriction enzyme is capable of cleaving said double-stranded DNA at a cleavage site separate from the recognition site therefor.

2. The method according to claim 1, wherein the double stranded DNA is double-stranded cDNA.

3. The method according to claim 1, wherein the double-stranded DNA is hemimethylated double-stranded cDNA or chemically synthesized double-stranded DNA.

4. The method according to claim 1, wherein the end(s) of the double-stranded DNA comprise(s) both a homopolymer and a non-homopolymer, and at least a portion of the non-homopolymer constitutes the recognition site for the restriction enzyme.

5. The method according to claim 1, wherein the homopolymer contained in the double-stranded DNA is an oligo dG:dC pair or an oligo dA:dT pair.

6. The method according to claim 1, wherein the class IIS restriction enzyme is selected from the group consisting of AlwI, AlwXI, Alw26I, BbsI, BbvI, BbvII, BcefI, BccI, BcgI, BciVI, BinI, BmrI, BpmI, BsaI, BseRI, BsgI, BsmAI, BsmBI, BspMI, BsrDI, BstF5I, EarI, Eco31I, Eco57I, Esp3I, FauI, FokI, GsuI, HgaI, HinGUII, HphI, Ksp632I, MboII, MmeI, MnlII, NgoVIII, PleI, RleAI, SapI, SfaNI, TaqII, Tth111II BsmI, BsrI, BsmFI and BseMII.

7. The method according to claim 1, wherein the double-stranded DNA is hemimethylated in a part of one strand other than the homopolymer.

8. The method according to claim 7, wherein the hemimethylation is introduced into cytosine or adenine.

9. The method according to claim 7, wherein the restriction enzyme is a restriction enzyme that does not act on double-stranded DNA that is hemimethylated at the recognition site or the cleavage site.

10. The method according to claim 9, wherein the restriction enzyme is a restriction enzyme that does not act on double-stranded DNA having a methyl group as the chemical modification.

11. The method according to claim 10, wherein the restriction enzyme is BbvI, HgaI or GsuI.

12. A method for determining a nucleotide sequence of double-stranded DNA utilizing one or both strands of the double-stranded DNA as a template, wherein the double-stranded DNA used as the template is double-stranded DNA prepared by the method according to claim 1.

13. The method according to claim 12, wherein the prepared double-stranded DNA is amplified by PCR or by using a microorganism, and the nucleotide sequence determination is performed by using the amplified double-stranded DNA as the template.

14. The method according to claim 12, wherein oligo dG:dC of the prepared double-stranded DNA has been partly or fully eliminated.

15. The method according to claim 13, wherein oligo dG:dC of the prepared double-stranded DNA has been partly or fully eliminated.

16. The method according to claim 12, wherein the nucleotide sequence determination is performed by forming a nucleic acid transcript of the double-stranded DNA in the presence of a terminator for nucleic acid transcription, and analyzing the resulting nucleic acid transcript.

17. The method according to claim 13, wherein the nucleotide sequence determination is performed by forming a nucleic acid transcript of the double-stranded DNA in the presence of a terminator for nucleic acid transcription, and analyzing the resulting nucleic acid transcript.

18. The method according to claim 16, wherein the nucleic acid transcription is performed by using an RNA polymerase.

19. The method according to claim 17, as wherein the nucleic acid transcription is performed by using an RNA polymerase.

* * * * *